(12) United States Patent
Wang et al.

(10) Patent No.: US 7,914,528 B2
(45) Date of Patent: Mar. 29, 2011

(54) ABLATION CATHETER TIP FOR GENERATING AN ANGLED FLOW

(75) Inventors: Huisun Wang, Maple Grove, MN (US); Jeremy D. Dando, Plymouth, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1124 days.

(21) Appl. No.: 11/647,346

(22) Filed: Dec. 29, 2006

(65) Prior Publication Data

US 2008/0161800 A1  Jul. 3, 2008

(51) Int. Cl.
*A61B 18/14* (2006.01)
(52) U.S. Cl. .......................................................... 606/41
(58) Field of Classification Search ............... 606/38–45
See application file for complete search history.

(56) References Cited

U.S. PATENT DOCUMENTS

| | | | |
|---|---|---|---|
| 5,056,517 A | 10/1991 | Fenici | |
| 5,230,349 A | 7/1993 | Langberg | |
| 5,348,554 A | 9/1994 | Imran et al. | |
| 5,423,811 A | 6/1995 | Imran et al. | |
| 5,462,521 A | 10/1995 | Brucker et al. | |
| 5,545,161 A | 8/1996 | Imran | |
| 5,643,197 A | 7/1997 | Brucker et al. | |
| 5,792,140 A | 8/1998 | Tu et al. | |
| 5,843,152 A | 12/1998 | Tu et al. | |
| 5,913,856 A | 6/1999 | Chia et al. | |
| 5,971,968 A * | 10/1999 | Tu et al. | 604/264 |
| 6,017,338 A | 1/2000 | Brucker et al. | |
| 6,080,151 A | 6/2000 | Swartz | |
| 6,120,476 A * | 9/2000 | Fung et al. | 604/95.04 |

(Continued)

FOREIGN PATENT DOCUMENTS

WO  WO2005/048858  6/2005

(Continued)

OTHER PUBLICATIONS

Wittkampf, et. al., "Radiofrequency Ablation With a Cooled Porous Electrode Catheter," JACC, vol. 11, No. 2, Feb. 1988:17A Abstracts.

*Primary Examiner* — Linda C Dvorak
*Assistant Examiner* — Amanda Scott
(74) *Attorney, Agent, or Firm* — Dykema Gossett PLLC

(57) ABSTRACT

The present invention provides an ablation catheter tip for use with an irrigated catheter device comprising an inner cavity and at least one passageway that leads to an orifice, wherein the fluid flow from the orifice promotes a circular, vortex, or spiral flow around the catheter tip from the acute angle formed at the orifice with respect to a line tangent to the surface of the ablation electrode at the orifice. The present invention further provides for an ablation catheter tip, for use with an irrigated catheter device, comprising an inner cavity and at least one curved passageway that leads to an orifice, wherein a line drawn tangent to the arc of the curve forms an acute angle measured with respect to a line drawn tangent to surface of the ablation electrode at the orifice of the passageway. Additionally, the present inventions provides a method for cooling an ablation catheter tip and a method for generating, with a low-volume irrigation flow, a rotational, spiral, or vortex flow around the ablation catheter tip.

30 Claims, 5 Drawing Sheets

U.S. PATENT DOCUMENTS

| | | |
|---|---|---|
| 6,120,500 A | 9/2000 | Bednarek |
| 6,210,406 B1 * | 4/2001 | Webster .......................... 606/41 |
| 6,602,242 B1 | 8/2003 | Fung et al. |
| 6,611,699 B2 | 8/2003 | Messing |
| 6,650,923 B1 | 11/2003 | Lesh et al. |
| 7,166,105 B2 | 1/2007 | Mulier et al. |
| 7,628,788 B2 * | 12/2009 | Datta .............................. 606/41 |
| 2003/0004506 A1 * | 1/2003 | Messing ........................ 606/41 |

FOREIGN PATENT DOCUMENTS

| | | | |
|---|---|---|---|
| WO | WO 2005048858 A1 * | 6/2005 | |
| WO | WO 2005074520 A2 * | 8/2005 | |

* cited by examiner

ABLATION CATHETER TIP FOR GENERATING AN ANGLED FLOW

BACKGROUND OF THE INVENTION a. Field of the Invention

The instant invention pertains generally to irrigated catheter devices. More particularly, the instant invention is directed toward ablation catheter tips for use in the human body, where an angled or a rotational irrigation fluid flow is generated around the ablation catheter tip, advantageously cooling the ablation electrode and targeted areas.

b. Background Art

Electrophysiology catheters are used for an ever-growing number of procedures. For example, catheters are used for diagnostic, therapeutic, and ablative procedures, to name just a few examples. Typically, a catheter is manipulated through the patient's vasculature and to the intended site, for example, a site within the patient's heart, and carries one or more electrodes, which may be used for ablation, diagnosis, or the like.

There are a number of methods used for ablation of desired areas, including for example, radiofrequency (RF) ablation. RF ablation is accomplished by transmission of radiofrequency energy to a desired target area through an electrode assembly to ablate tissue at the target site. Because RF ablation may generate significant heat, which if not controlled can result in excessive tissue damage, such as steam pop, tissue charring, and the like, it is desirable to include a mechanism to irrigate the target area and the device with biocompatible fluids, such as saline solution. The use of fluid mitigates rising temperature in and around the ablation electrode, therefore reducing the risk of unwanted tissue damage and blood coagulation.

There are typically two classes of irrigated catheter devices, open and closed ablation catheters. Closed ablation catheters typically circulate a cooling fluid within the inner cavity of the ablation catheter tip. Open ablation catheters, on the other hand, use the inner cavity of the ablation catheter tip as a manifold to distribute saline solution, or other irrigation fluids known to those skilled in the art, to one or more passageways leading to an orifice. This lowers the temperature of the ablation catheter tip by bringing the outer surface of the ablation electrode in contact with the cool irrigation fluid and dilute the blood around the electrode to prevent blood coagulation.

Because the velocity or volume flow rate of the irrigation flow is typically within the range of two milliliters per minute to twenty milliliters per minute and is thus relatively low compared to, for example, the velocity of the blood circulation inside the atrium of the heart, cooling is most effective when the irrigation flow is kept in the area close to the ablation catheter tip and accordingly the ablation electrode. However, in prior art embodiments, it was difficult to keep the flow close to the ablation electrode, as the flow was directed along a radial line away from the ablation catheter tip, therefore limiting the ability to cool. Thus, it is one object of the present invention to improve the cooling effect of irrigated catheters devices by, for example, generating an angled flow or rotational flow around the outer surface of the ablation catheter tip such that irrigation fluid is delivered, and remains, closer to the outer surface of the ablation electrode than in prior art embodiments. It is another object of the present invention to improve the cooling effect of irrigated catheter devices by insulating the irrigating chambers.

BRIEF SUMMARY OF THE INVENTION

The present invention is directed to improved ablation catheter tips and methods useful in conjunction with irrigated catheter devices and other ablation catheters.

The present invention provides for an ablation catheter tip, for use with an irrigated catheter device, having an inner cavity and at least one passageway that leads to an orifice at the catheter tip for allowing fluid flow. In one aspect, the invention provides for an ablation catheter tip for use with an irrigated catheter device wherein the fluid flow from one or more orifice promotes a circumferential, vortex, or spiral flow around the catheter tip. The present invention further provides for an ablation catheter tip, for use with an irrigated catheter device, comprising an inner cavity and at least one curved passageway that leads to an orifice. Additionally, the present invention provides a method for cooling an ablation catheter tip and a method for generating, with a low-velocity irrigation flow, a rotational, spiral, or vortex flow around the ablation catheter tip.

In another aspect, the design of the passageways and orifices to promote fluid flow uses acute angles with respect to the surface of the catheter tip, wherein a line radially extending outward from the orifice forms an acute angle measured with respect to a line drawn tangent to the outer surface of the ablation electrode. Thus, the fluid exiting from the orifice flows along a trajectory closer to the outer surface of the ablation electrode than in prior embodiments that direct the exiting flow away from or essentially directly out from an ablation catheter tip. Alternatively or additionally, the passageways and orfices can be angled toward or away from an ablation catheter tip.

The ablation catheter tip of the present invention is made of materials available to one skilled in the art, including but not limited to platinum or platinum alloys containing iridium. For example, in one embodiment, the ablation catheter tip is made of a platinum alloy that contains ten percent iridium. In another embodiment, the ablation catheter tip contains proximal and distal members, each made of different materials. In that embodiment, the proximal member is comprised of a poor thermally conductive material selected from the group consisting of HDPE, polyimide, polyaryletherketones, polyetheretherketones, polyurethane, polypropylene, oriented polypropylene, polyethylene, crystallized polyethylene terephthalate, polyethylene terephthalate, polyester, ceramics, and plastics such as Delrin®, and mixtures thereof. The distal member is comprised of an electrically, and potentially thermally, conductive material selected from the group consisting of platinum, gold, iridium, palladium, stainless steel, and mixtures thereof. In certain embodiments, a poor thermally conductive material or materials can be incorporated into a part or all of the catheter tip, and such materials and insulating functions and effects are disclosed in co-pending U.S. application Ser. No. 11/434,220, the content of which is hereby incorporated by reference in its entirety.

In one embodiment of the present invention, the passageways are elongated. In yet another embodiment, the passageways are curved. In either embodiment, at least one and optionally all of the passageways may be constructed of or lined with the poor thermally conductive materials disclosed above, or any other insulated material known to those of skill in the art. In one embodiment the inner cavity is circular. In another embodiment, the inner cavity is polygonal. In yet another embodiment, the inner cavity contains one or more chambers.

The present invention further includes a method for improved cooling of ablation catheter tips and a method for generating, with a low velocity or low volume flow rate—for example, in the range of two milliliters per minute to twenty milliliters per minute—irrigation flow, a rotating flow around an ablation catheter tip. The method for cooling an ablation catheter tip comprises: delivering a fluid to an inner cavity of an ablation catheter tip and then delivering the fluid into at least one passageway that leads to an orifice, wherein the fluid the exits the orifice at an acute angle measured with respect to a line drawn tangent to the surface of the ablation electrode. The method for generating, with a low-velocity irrigation flow, a rotating, spiral, or vortex flow around an ablation catheter tip comprises: delivering a fluid to an inner cavity of an ablation catheter tip and then delivering the fluid into at least one passageway that leads to an orifice, wherein the fluid exits the orifice at an acute angle measured with respect to a line drawn tangent to the surface of the ablation electrode.

The foregoing and other aspects, features, details, utilities, and advantages of the present invention will be apparent from reading the following description and claims, and from reviewing the accompanying drawings.

DETAILED DESCRIPTION OF THE INVENTION

The headings (such as "Brief Summary") used are intended only for general organization of topics within the disclosure of the invention and are not intended to limit the disclosure of the invention or any aspect of it. In particular, subject matter disclosed in the "Background Art" includes aspects of technology within the scope of the invention and thus may not constitute solely background art. Subject matter disclosed in the "Brief Summary" is not an exhaustive or complete disclosure of the entire scope of the invention or any particular embodiment.

As used herein, the words "preferred," "preferentially," and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention and no disclaimer of other embodiments should be inferred from the discussion of a preferred embodiment or a figure showing a preferred embodiment.

Figure 1:
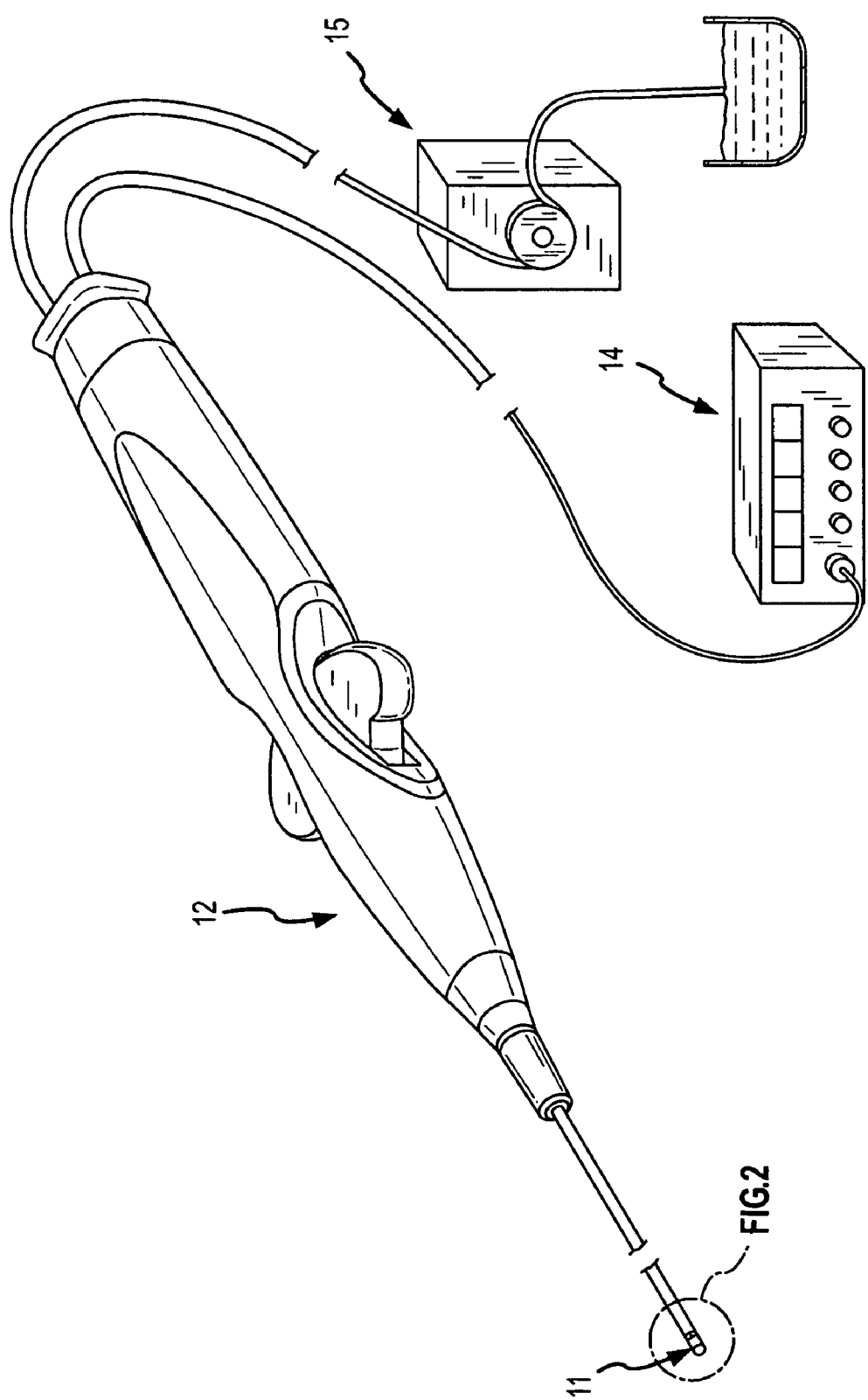
FIG. 1 depicts a system or device for irrigating using an ablation catheter tip of the invention.
Figure 2A:
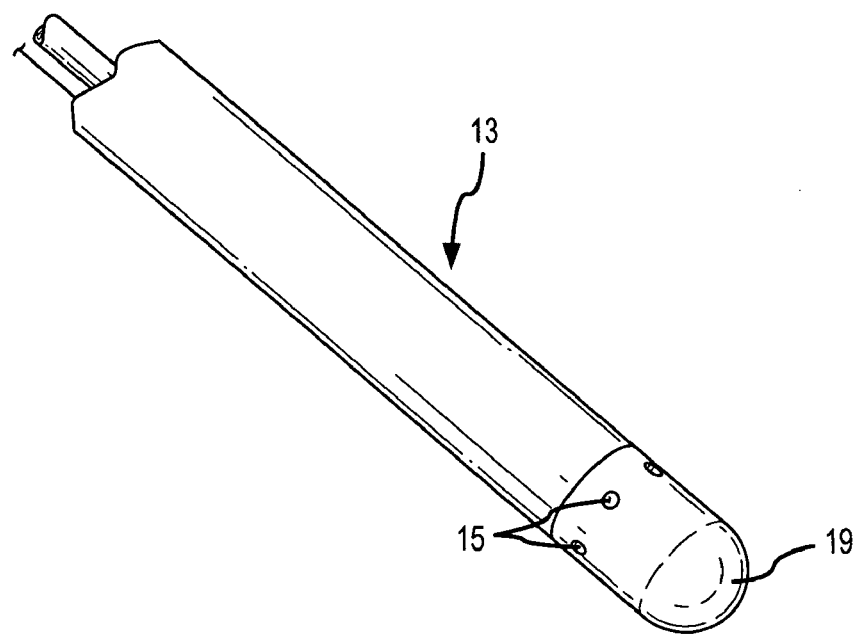
FIG. 2a is an enlarged, isometric view of an irrigated electric embodiment of an ablation catheter tip of the invention.
Figure 2B:
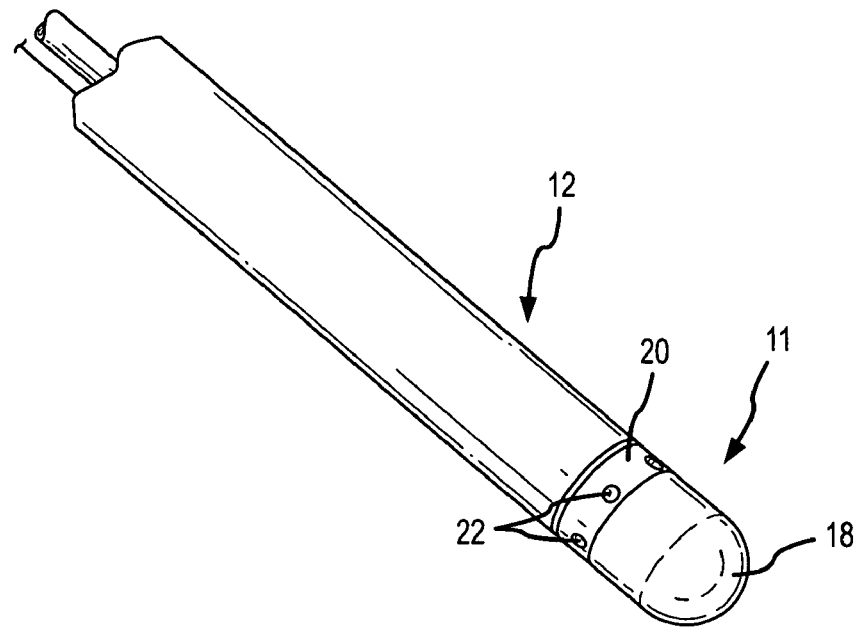
FIG. 2b is an enlarged, isometric view of a separated or insulated irrigation electrode embodiment of an ablation catheter tip of the invention.

In FIG. 1 the catheter tip 11 is operably connected to the distal end of a hand-held device 12, which is operably connected to an RF generator 14 and a pump 15 for irrigation fluid. FIGS. 2a and 2B depict two general embodiments; a conventional irrigated ablation catheter tip design of FIG. 2a, and a multi-part or separated ablation catheter tip of FIG. 2b. In the isometric view of FIG. 2a, a tip electrode 19 includes irrigation orifices 15 and is connected to a proximal region 13 of catheter tip. In the isometric view of FIG. 2b, the ablation catheter tip 11 includes orifices 22 in a separated, optionally insulated, manifold region 20 between proximal shaft region 12 and tip electrode 18.

Figure 3:
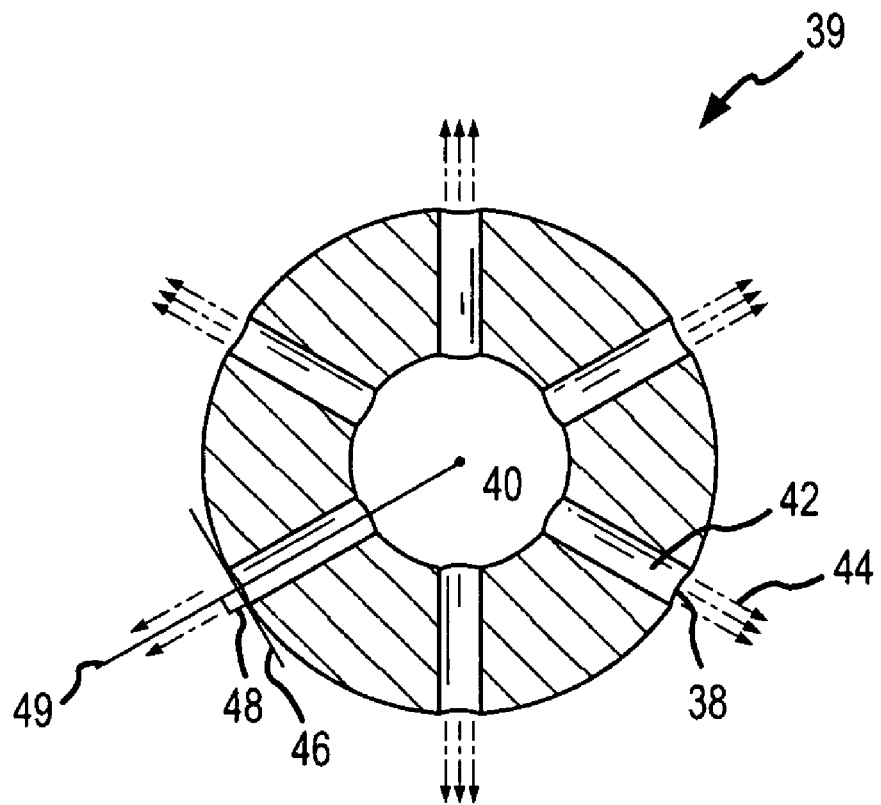
FIG. 3 is a cross-sectional view of a prior art irrigated ablation catheter tip.

FIG. 3 is a cross-sectional view of a prior art irrigated ablation catheter tip. The tip 39 contains a circumferential inner cavity 40 connected to passageways 42 leading to orifices 38. An imaginary line 49 radially extends from the center of the cavity and through orifice 38. Irrigating fluid travels through the inner cavity 40 and into the passageways 42, at which point the fluid exits the tip 39 through orifices 38. The flow 44 of the exiting fluid forms a right angle 48 measured with respect to a line 46 drawn tangent to the surface of the ablation electrode at the orifice 38.

Figure 4:
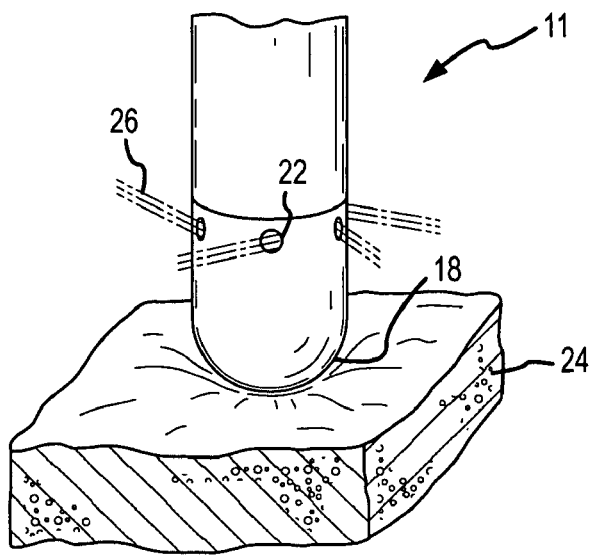
FIG. 4 is an isometric view of an ablation catheter tip of the invention in contact with target tissue.
Figures 5, 6:
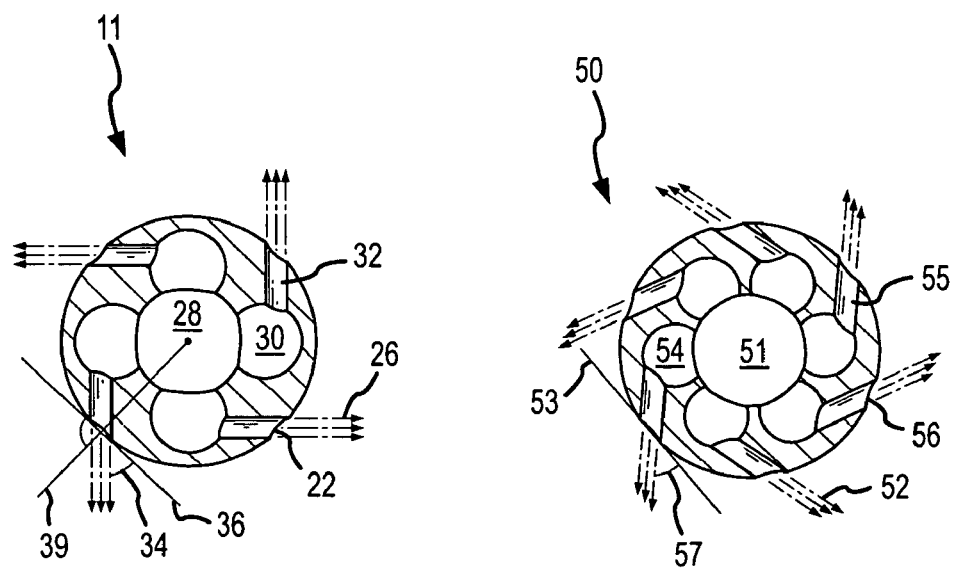
FIGS. 5-9 are cross-sectional views of various angled flow and inner cavity design embodiments of the invention

FIG. 4 is an isometric view of an ablation catheter tip 11 according to the invention depicted in use contacting tissue. The distal end 18 includes an ablation electrode and is in contact with tissue 24 to perform an ablation procedure. Exiting from each orifice 22 is an angled flow 26 of saline solution, for example. FIGS. 5-9 are cross-sectional views of ablation catheter tips according to various embodiments of the angled passageways, orifices, and inner cavity designs of the invention. In FIGS. 5-6, the inner cavities 28 and 51 are circular and include chambers 30 and 54, respectively. Protruding from each chamber are elongated passageways 32 or 55 leading to orifices 22 or 56. The chambers and elongated passageways are considered to be in fluid communication as irrigation fluid can flow from an inner cavity to a passageway, and ultimately flow out an orifice on the surface of the catheter. Fluid flows 26 and 52 exit from orifices 22 and 56 and form acute angles 34 and 57, measured with respect to lines 36 and 53 drawn tangent to outer surface of the ablation electrode at the orifice. The passageways need not lie on a plane perpendicular to the axis of the catheter tip, but may be angled relative to the plane, for instance, toward or away from the distal end of the catheter tip.

Figure 7:
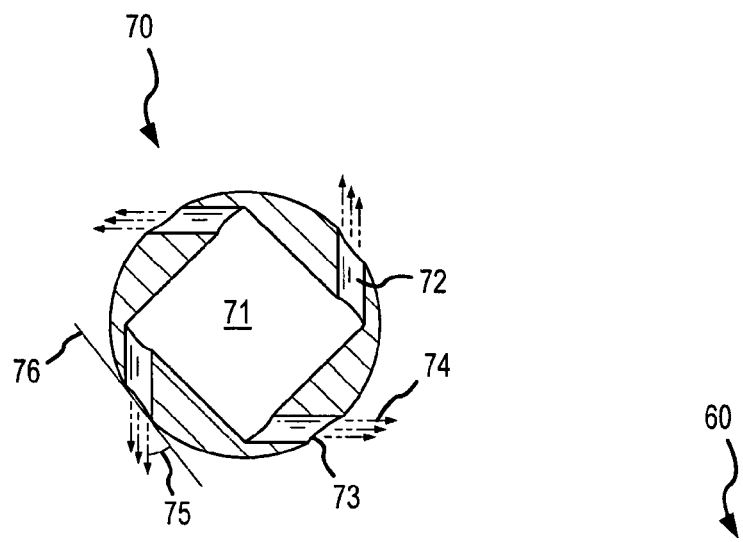

FIG. 7 is a cross-sectional view of an ablation catheter tip 70 according to the claimed invention. The inner cavity 71 is polygonal. Connected to the inner cavity are four passageways 72, each leading to orifices 73. A fluid flow 74 exits from each orifice 73 and forms an acute angle 75 measured with respect to an imaginary line 76 drawn tangent to the outer surface of the ablation electrode.

Figure 8:
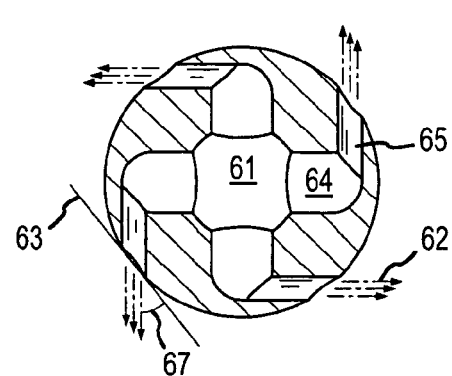

FIG. 8 is a cross-sectional view of an ablation catheter tip 60 according to the claimed invention. The inner cavity 61 is polygonal and contains attached chambers 64. Connected to each chamber 64 is a passageway 65 leading to orifices 66. A fluid flow 62 exits from each orifice 66, forming an acute angle 67 measured with respect to an imaginary line 63 drawn tangent to the outer surface of the ablation electrode.

Figure 9:
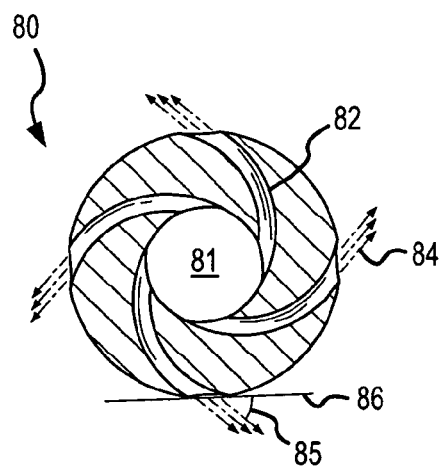

FIG. 9 is an ablation catheter tip 80 according to the claimed invention. The inner cavity 81 is circular and the passageways leading to orifices 83 are curved. A fluid flow 84 exits from each orifice 83 and forms an acute angle 85 measured with respect to an imaginary line 86 drawn tangent to the outer surface of the ablation electrode, and promotes a vortex flow of fluid around the ablation electrode and catheter.

The various exemplary embodiments and options available to one of skill in the art will now be discussed in more detail. FIG. 1 is an isometric view of an ablation catheter tip 11 operably connected to the distal end of a hand-held irrigated catheter device 12, which is operably connected to an RF generator 14 and a pump 15. The structural and functional features of the hand-held device 12, the RF generator assembly 14, and pump assembly 15 are well-known to those of skill in the art. For example, the RF generator can be St. Jude Medical's IBI-1500T6 Cardiac Ablation Generator or any other RF generator assembly known to those of skill in the art. Likewise, the pump assembly can be any known assembly, including fixed volume rolling pumps, variable volume syringe pumps, and any other pump assembly known to those of skill in the art.

FIG. 2a is an isometric view of an ablation catheter tip 19 connected to the shaft of a hand-held irrigated catheter device 13. The tip includes passageways 15 for delivering irrigation fluid to the outer surface of the catheter tip and targeted tissue area.

FIG. 2b is an isometric view of an ablation catheter tip 11 connected to the shaft of a hand-held irrigated catheter device 12. In this embodiment, the tip includes ablation electrode 18, positioned at the distal end of tip 11, manifold or proximal region 20, and passageways 22 for delivering irrigation fluid to the outer surface of the catheter tip and targeted tissue area. The distal end is comprised of any electrically, and potentially thermally, conductive material known to those of ordinary skill in the art for delivery of ablative energy to target tissue areas. Examples of the thermally conductive material include gold, platinum, iridium, palladium, stainless steel, and any mixtures thereof. Moreover, there are a number of electrode designs contemplated within the scope of the present invention including tip electrodes, ring electrodes, and any combination thereof. The manifold region is comprised of poor thermally conductive material. A poor thermally conductive material is one with physical attributes that decreases heat transfer from the passageway(s) 22 to the ablation electrode 18 positioned at distal end by about 10% or more, and more preferably by about 25% or more measured by known methods to one of ordinary skill in the art. In particular embodiments, materials that decreased heat transfer by more than approximately 75% performed favorably. It is further contemplated that a poor thermally poor thermally conductive material could have physical attributes that decrease heat transfer less than about 10%, provided that the remaining structural components are selected with the appropriate characteristics and sensitivities to maintain adequate monitoring and control of the process. Thus, while these properties are preferred, the poor thermally conductive material may be any material known to one of skill in the art consistent with the spirit of the invention. Examples of poor thermally conductive materials useful in conjunction with the present invention include, but are not limited to, HDPE, polyimides, polyaryletherketones, polyetheretherketones, polyurethane, polypropylene, oriented polypropylene, polyethylene, crystallized polyethylene terephthalate, polyethylene terephthalate, polyester, ceramics, and plastics such as Delrin®, and mixtures thereof.

Referring now to FIG. 4, an ablation catheter tip 11 according to the present invention is disclosed in greater detail. The tip 11 is connected to the shaft of a hand-held irrigated catheter device 12 and is ablating targeted tissue area 24. Three orifices 22, producing three angled flows 26, are visible. The angle of the flow, in the present invention and in prior art embodiments, relates to the angle of the orifices and passageways. In prior art embodiments, such as the embodiment depicted in FIG. 3, a line 49 may be drawn from the center of the inner cavity 48 extending radially through a passageway 42 and orifice 38 to form a right angle 48 with a line 46 drawn tangent to the outer surface of the ablation electrode. Accordingly, the flow 44 exits the orifice normal to the tip and the cooling capacity is limited, since the flow is being directed away from the tip and thus away from the ablation electrode. By contrast, in the claimed invention, such as the embodiment depicted in FIG. 5, a line 39 radially extending from the center of the inner cavity 28 through an orifice 22 to form a right angle with a line 36 drawn tangent to the surface of the ablation electrode does not also radially extend through the passageway 32. As a result, the flow 26 exits the passageway through orifice at an acute angle 34 measured with respect to line 36. By directing the irrigation flow at an acute angle, the flow stays close to, and rotates around, the typically cylindrical outer surface of the catheter tip, therefore increasing cooling.

One skilled in the art will recognize that acute angle 34 can be any number of pre-determined angles. In theory, any acute angle between one degree and eighty-nine degrees is feasible. In practice, and due to a variety of factors, including but not limited to catheter diameter, passageway diameter, outlet size, fluid flow properties, and manufacturing considerations, the acute angle should be between 20 and 70 degrees, and preferably between 30 and 60 degrees, as depicted in the FIGS. 5-9.

The ablation catheter tip depicted in FIG. 5 further contains four chambers 30, connected to the inner cavity 28 and passageways 32. The chambers allow the passageways and orifices to be positioned, without significantly altering the size of the inner cavity or length of the passageways, such that exiting flows achieve smaller angles 34, therefore keeping the exiting flow closer to the electrode assembly, than otherwise possible in embodiments of the same-sized inner cavity and passageways. The ablation catheter tip depicted in FIG. 6 contains many of the same features as the assembly depicted in FIG. 5, however, it contains six chamber 54, six passageways 55, and six orifices 56. One skilled in the art readily recognizes that the claimed invention is not limited to designs with four or six chambers, passageways, or orifices, as depicted in FIGS. 5 and 6 respectively.

Referring now to FIG. 7, an ablation catheter tip 70 with a square, i.e. polygonal, inner cavity 71 is depicted. In FIG. 8, chambers 64 are used in conjunction with a polygonal inner cavity 61.

The embodiment of the claimed invention depicted in FIG. 9 contains curved passageways 82. The curved passageways 82 can be used in conjunction with a circumferential inner cavity 81, as depicted, with polygonal inner cavities, or with any other conceivable shapes, and with or without chambers. The curved passageways cause the irrigating fluid. 84 to exit at a smaller angle 85 and therefore remain closer the outer surface of the electrode assembly that in assemblies with similarly sized cavities or passageways.

Although various embodiments of this invention have been described above with a certain degree of particularity, those skilled in the art could make numerous alterations to the disclosed embodiments without departing from the spirit or scope of this invention. Additionally, all directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method for cooling an ablation catheter tip, the method comprising: delivering a fluid to an inner cavity of the tip and delivering the fluid to at least one passageway that leads to an orifice at the surface of the catheter tip, wherein the fluid exits the orifice at an acute angle measured with respect to a line drawn tangent to the surface of the ablation electrode at the orifice.

2. The method of claim 1, wherein the fluid is delivered to a plurality of passageways and a plurality of orifices, whereby the fluid from the orifices creates a circumferential or spiral flow around the circumference of a region of the catheter tip.

3. The method of claim 1, wherein the fluid is delivered to an inner cavity that is circular.

4. The method of claim 1, wherein the fluid is delivered to an inner cavity that is polygonal.

5. The method of claim 1, wherein the fluid is delivered to an inner cavity that additionally contains at least one chamber.

6. The method of claim 1, wherein the fluid further exits the tip in the direction of the distal end of said tip.

7. A method for generating, with an irrigation flow, a rotating flow around the an ablation catheter tip, the method comprising: delivering a fluid to an inner cavity of said tip and delivering said fluid into at least one passageway that leads to an orifice, wherein said fluid exits the orifice at an acute angle measured with respect to a line drawn tangent to the surface of the ablation electrode at the orifice.

8. The method of claim 7, wherein the fluid is directed into a plurality of passageways.

9. The method of claim 7, wherein the fluid is delivered to an inner cavity that is circular.

10. The method of claim 7, wherein the fluid is delivered to an inner cavity that is polygonal.

11. The method of claim 7, wherein the fluid is delivered to an inner cavity that additionally contains at least one chamber.

12. The method of claim 7, wherein the fluid further exits the tip in the direction of the distal end of said assembly.

13. The method of claim 7, wherein said irrigation flow exits the orifice with a volume in the range of about 2 milliliters per minute to about 20 milliliters per minute.

14. An ablation catheter tip, for use with an irrigated catheter device, comprising an inner cavity and at least one curved passageway that leads to an orifice, wherein a line drawn tangent to the arc of the curve forms an acute angle measured with respect to a line drawn tangent to circumferential surface of an ablation electrode at the orifice, and wherein the inner cavity includes a center cavity in fluid communication with a plurality of separate chambers, and one of the plurality of separate chambers is in fluid communication with the at least one passageway.

15. The ablation catheter tip of claim 14, wherein multiple curved passageways lead to multiple orifices.

16. An ablation catheter tip, for use with an irrigated catheter device, comprising an inner cavity and at least one passageway that leads to an orifice on the catheter tip surface, wherein a line extending from the center of the orifice and in the direction of the flow of fluid out of the orifice forms an acute angle measured with respect to a line drawn tangent to the circumferential surface of the catheter tip at the orifice, and wherein the inner cavity includes a center cavity in fluid communication with a plurality of separate chambers, and one of the plurality of separate chambers is in fluid communication with the at least one passageway.

17. The ablation catheter tip of claim 16, wherein said tip contains a plurality of passageways to a plurality of orifices.

18. The ablation catheter tip of claim 17, wherein the orifices are symmetrically spaced.

19. The ablation catheter tip of claim 16, wherein the inner cavity is circumferential.

20. The ablation catheter tip of claim 16, wherein the inner cavity forms a polygon.

21. The ablation catheter tip of claim 16, wherein the inner cavity includes a center cavity fluidly coupled to at least one chamber which is fluidly coupled to the at least one passageway that leads to the orifice.

22. The ablation catheter tip of claim 16, wherein the inner cavity includes a center cavity in fluid communication with a plurality of chambers, which in turn are in fluid communication with a plurality of corresponding passageways that lead to orifices on the catheter tip surface.

23. The ablation catheter tip of claim 16, wherein the acute angle is between about 30 and about 60 degrees.

24. The ablation catheter tip of claim 16, wherein the at least one passageway is curved.

25. The ablation catheter tip of claim 16, wherein the passageway is angled towards the distal end of said ablation catheter tip.

26. The ablation catheter tip of claim 16, wherein the passageway is insulated with a poor thermally conductive material.

27. The ablation catheter tip of claim 16, wherein said tip is made of platinum or a platinum alloy containing iridium.

28. The ablation catheter tip of claim 27, wherein the platinum alloy contains up to ten percent iridium.

29. The ablation catheter tip of claim 16, wherein an ablation electrode is in a distal region of said tip and the orifices are in a distal region of said tip.

30. The ablation catheter tip of claim 29, wherein the distal region is made of electrically and thermally conductive material and a proximal region is made of poor thermally conductive material.

* * * * *